United States Patent
Meinke et al.

(10) Patent No.: US 9,826,996 B2
(45) Date of Patent: Nov. 28, 2017

(54) SYSTEMS AND METHODS WHICH REMOVE MATERIAL FROM BLOOD VESSEL WALLS

(75) Inventors: Rainer Meinke, Melbourne, FL (US); Sasha Ishmael, Melbourne, FL (US)

(73) Assignee: Advanced Magnet Lab, Inc, Palm Bay, FL (US)

( * ) Notice: Subject to any disclaimer, the term of this patent is extended or adjusted under 35 U.S.C. 154(b) by 587 days.

(21) Appl. No.: 13/982,784

(22) PCT Filed: Jan. 31, 2012

(86) PCT No.: PCT/US2012/023271
§ 371 (c)(1),
(2), (4) Date: Jul. 31, 2013

(87) PCT Pub. No.: WO2012/106306
PCT Pub. Date: Aug. 9, 2012

(65) Prior Publication Data
US 2013/0310626 A1  Nov. 21, 2013

Related U.S. Application Data

(60) Provisional application No. 61/438,198, filed on Jan. 31, 2011.

(51) Int. Cl.
*A61B 17/22* (2006.01)
*A61N 2/00* (2006.01)
(Continued)

(52) U.S. Cl.
CPC .......... *A61B 17/22012* (2013.01); *A61N 1/32* (2013.01); *A61N 2/004* (2013.01);
(Continued)

(58) Field of Classification Search
CPC . A61N 1/32; A61N 1/40; A61N 2/004; A61N 2/02; A61B 17/22012
See application file for complete search history.

(56) References Cited

U.S. PATENT DOCUMENTS

| 3,915,151 A | 10/1975 | Kraus |
| 4,838,850 A * | 6/1989 | Rosengart .............. A61N 2/002 600/14 |

(Continued)

FOREIGN PATENT DOCUMENTS

| EP | 62032 | 1/2007 |
| GB | 871672 | 6/1961 |

*Primary Examiner* — Michael Carey
*Assistant Examiner* — Natasha Patel
(74) *Attorney, Agent, or Firm* — Stephen C. Thomas; Ferdinand M. Romano

(57) ABSTRACT

Systems and methods for removing plaque from blood vessels by applying constant or time varying magnetic or electrical fields. In one embodiment a system includes winding configurations positioned about a central axis along which a body region may be placed. Each winding configuration generates a magnetic field in a direction which passes through the body region. A first winding configuration generates a first magnetic field component perpendicular to a second magnetic field component generated by a second winding configuration. In a related method for removing a deposit of plaque from a position along a wall of a blood vessel a magnetic field is applied which has a net direction predominantly orthogonal to the direction of the flow of blood through the vessel.

6 Claims, 5 Drawing Sheets

(51) Int. Cl.
*A61N 2/02* (2006.01)
*A61N 1/32* (2006.01)
A61N 1/40 (2006.01)
A61B 18/00 (2006.01)

(52) U.S. Cl.
CPC ...... *A61N 2/02* (2013.01); *A61B 2017/22081* (2013.01); *A61B 2018/00386* (2013.01); *A61B 2018/00404* (2013.01); *A61N 1/40* (2013.01)

(56) References Cited

U.S. PATENT DOCUMENTS

| | | |
|---|---|---|
| 4,889,526 A | 12/1989 | Rauscher et al. |
| 5,245,988 A * | 9/1993 | Einars .................... G10K 15/06 |
| | | 181/120 |
| 5,254,112 A * | 10/1993 | Sinofsky ............ A61B 5/02007 |
| | | 600/439 |
| 5,470,352 A * | 11/1995 | Rappaport ............. A61B 18/18 |
| | | 606/194 |
| 6,921,042 B1 | 7/2005 | Goodzeit et al. |
| 2006/0064082 A1* | 3/2006 | Bonutti .................... A61N 7/00 |
| | | 606/32 |
| 2006/0142632 A1 | 6/2006 | Meretei |
| 2006/0142749 A1* | 6/2006 | Ivkov ................ A61K 41/0052 |
| | | 606/27 |
| 2008/0262341 A1 | 10/2008 | Boyden et al. |
| 2009/0085710 A1 | 4/2009 | Meinke |
| 2010/0259259 A1* | 10/2010 | Zahn ................. G01R 33/5601 |
| | | 324/309 |

* cited by examiner

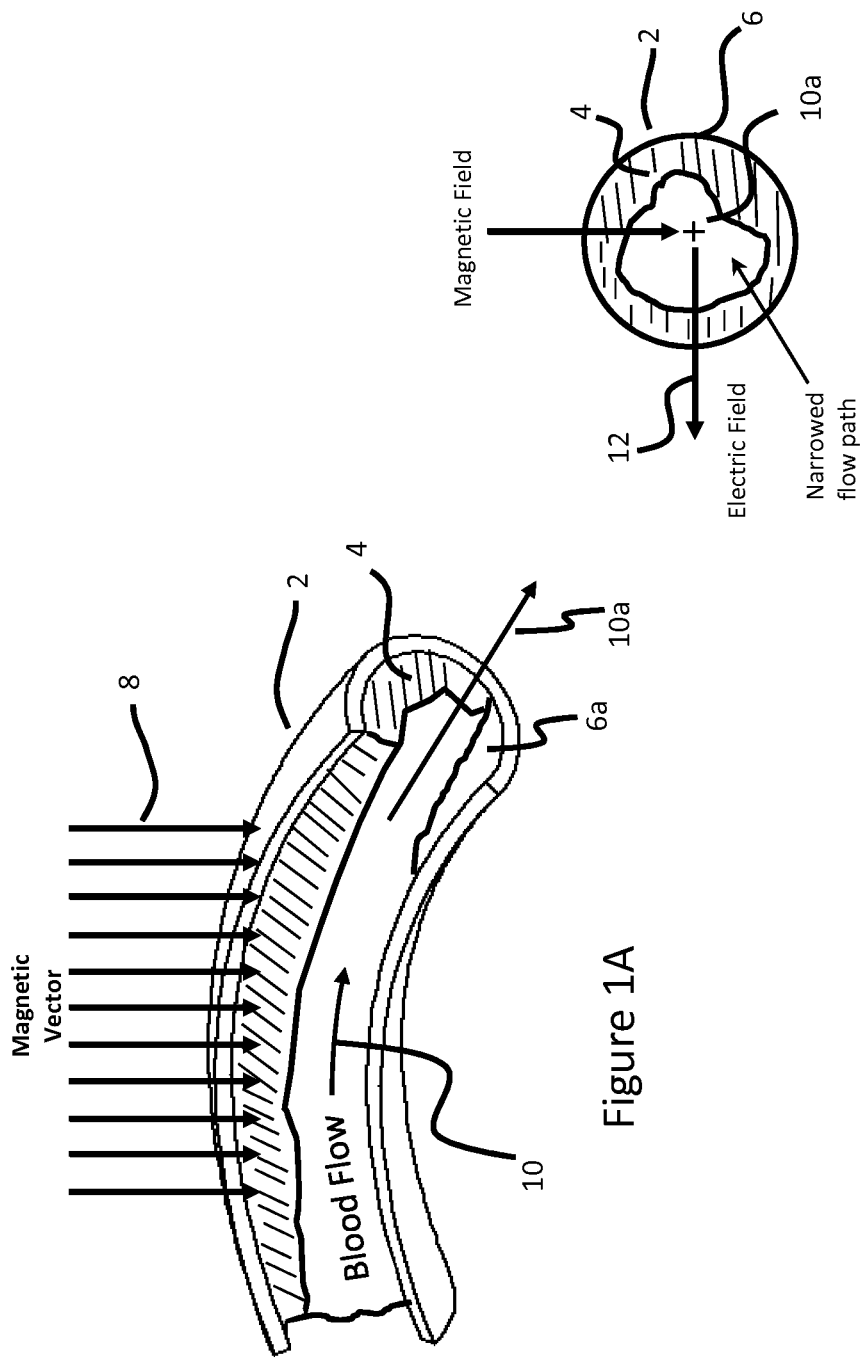

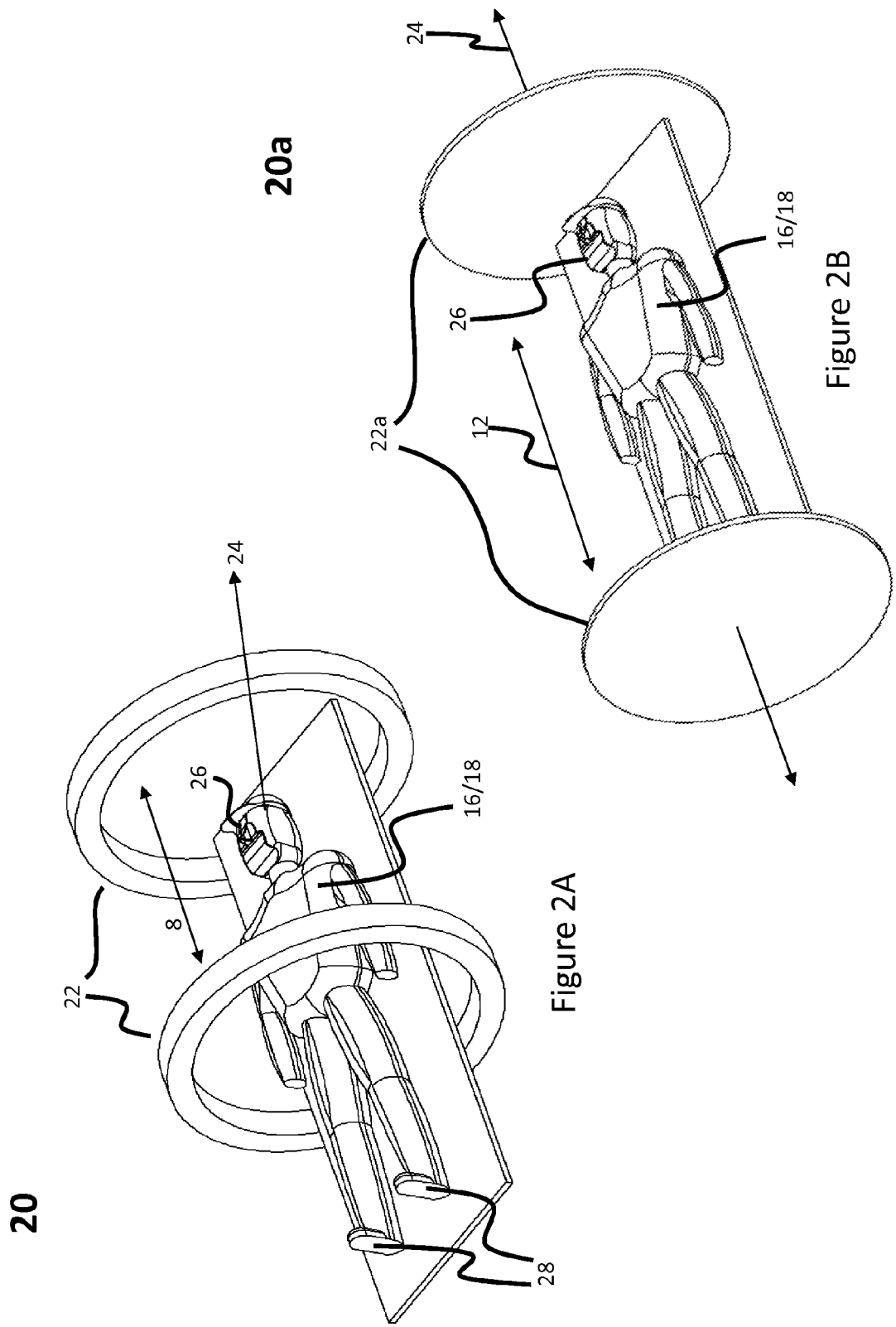

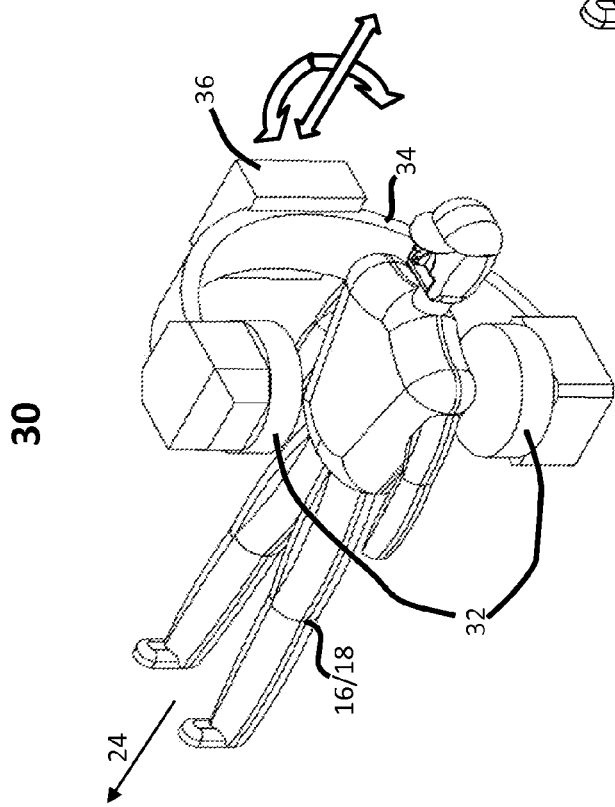
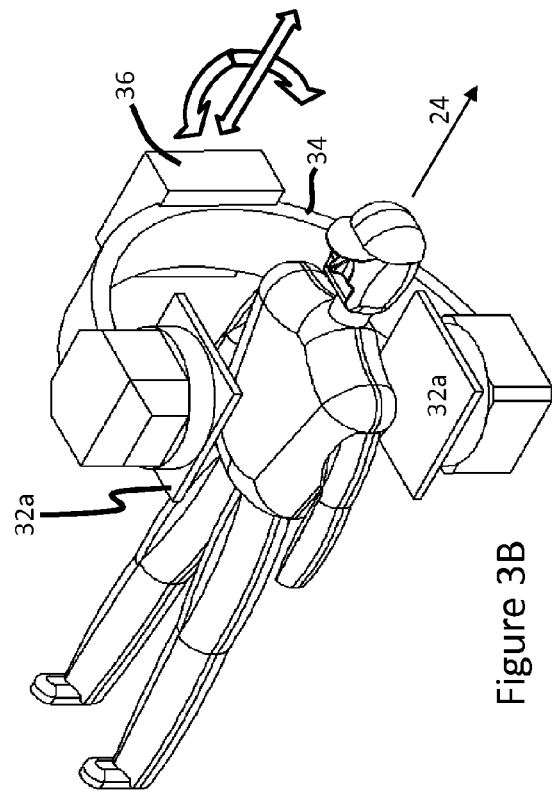
Figure 3A
Figure 3B

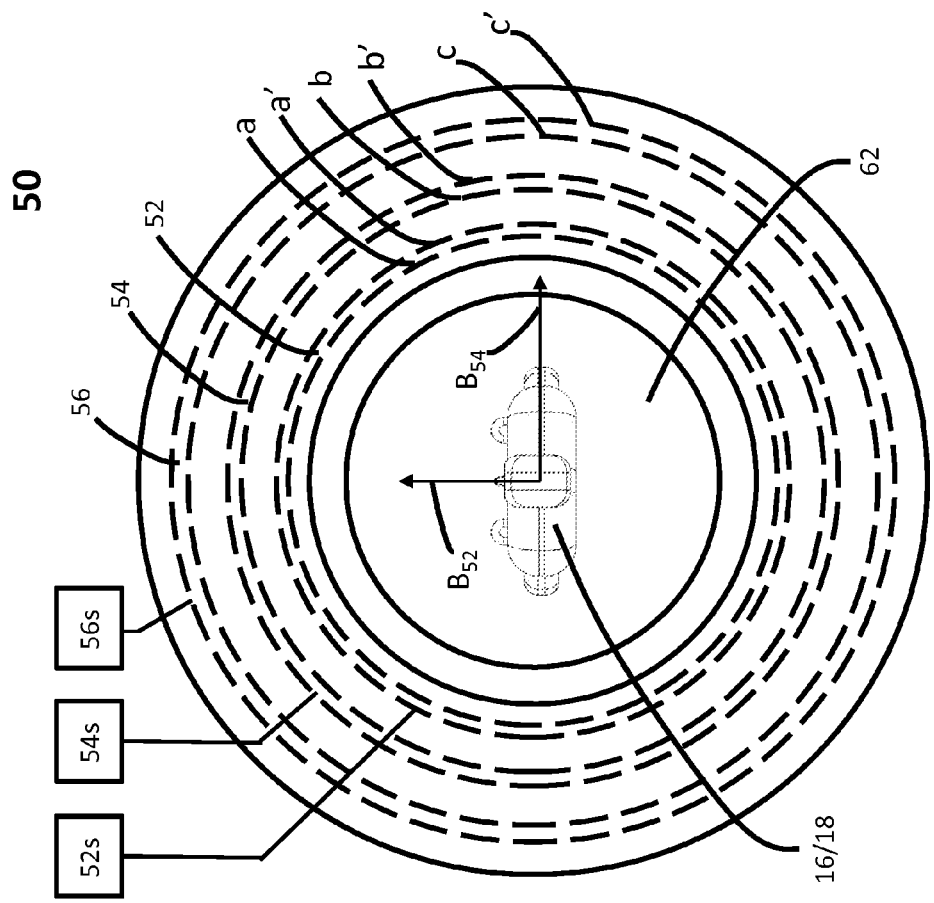
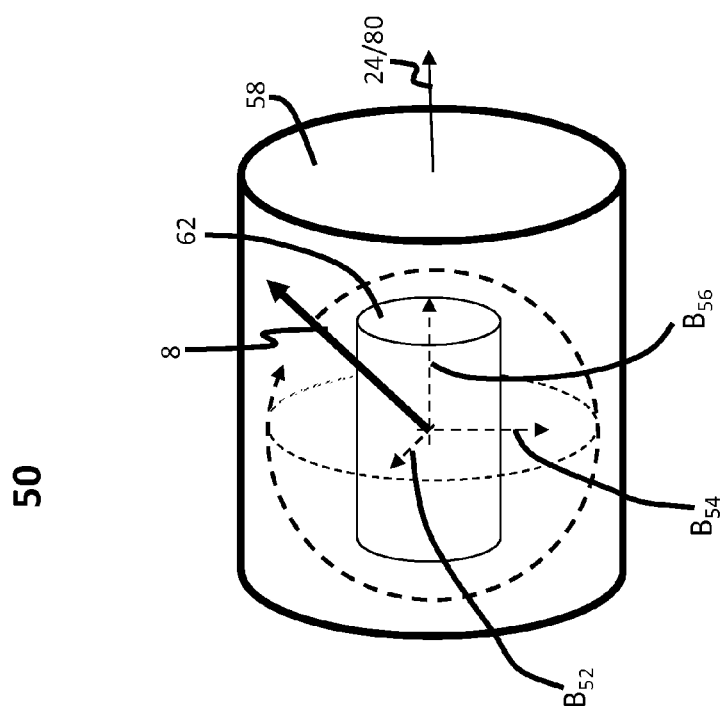
Figure 4A
Figure 4B

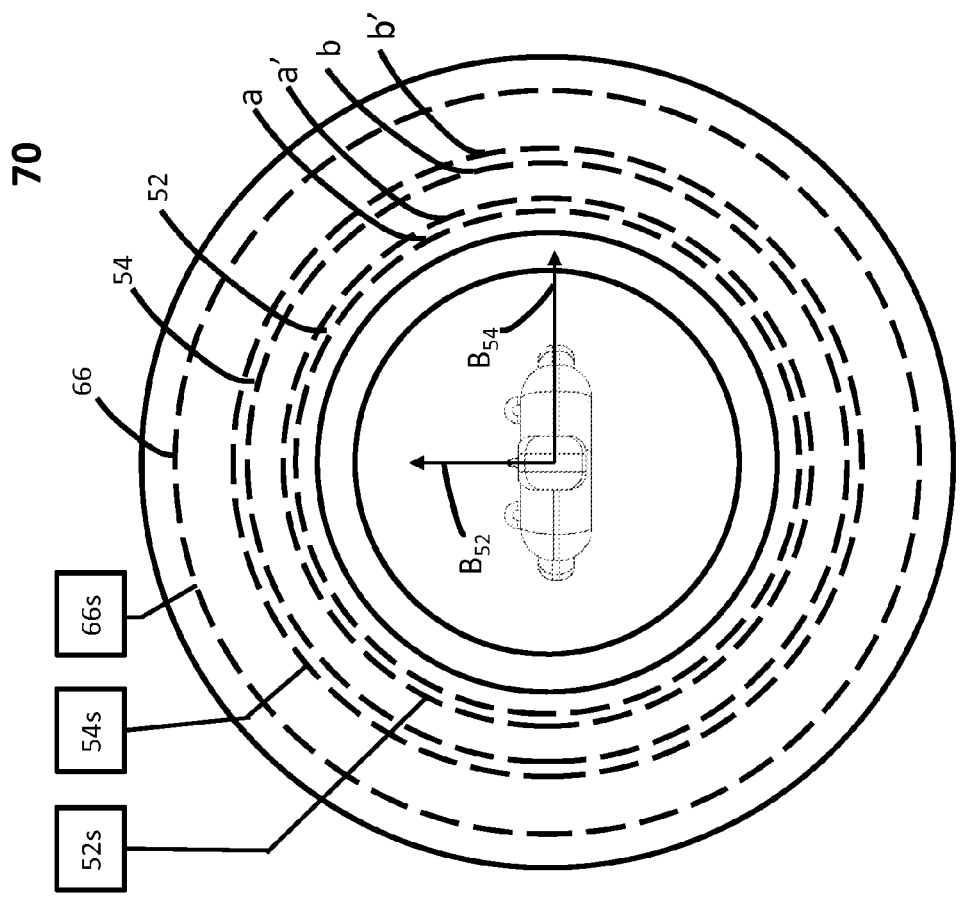
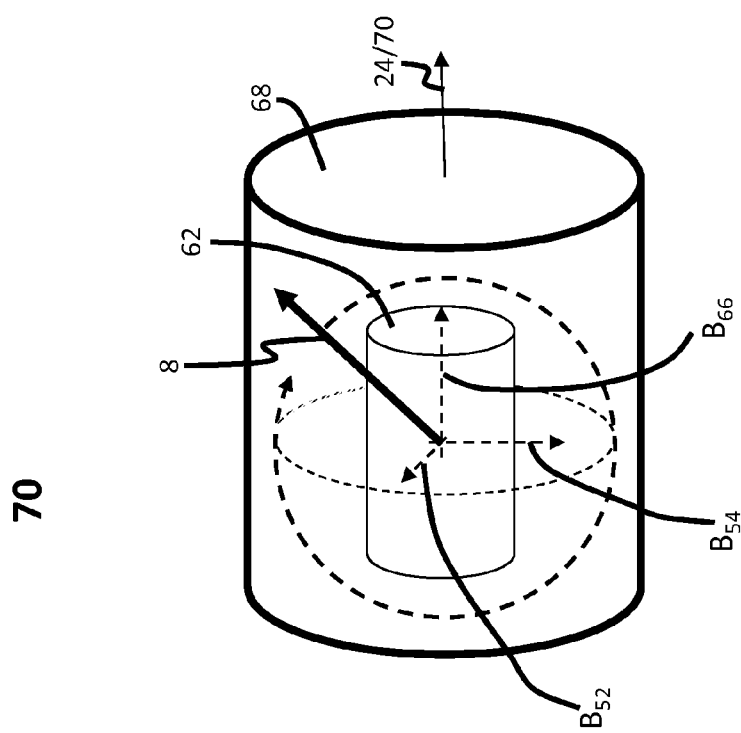
Figure 5A
Figure 5B

SYSTEMS AND METHODS WHICH REMOVE MATERIAL FROM BLOOD VESSEL WALLS

PRIORITY BASED ON RELATED APPLICATION

This application is filed as the National Stage application which claims priority based on PCT Application No. PCT/US2012/023271 filed Jan. 31, 2012 and U.S. application Ser. No. 13/362,503 filed Jan. 31, 2012 and U.S. Provisional Application No. 61/438,198 filed Jan. 31, 2011.

FIELD OF THE INVENTION

The present invention relates to medical methods and systems and, more particularly, to removal of deposits from blood vessels in cardio-vascular systems.

BACKGROUND

Peripheral and coronary blockages are caused by deposits of fatty substances, e.g., cholesterol, cellular waste products, calcium and fibrin (a clotting material in the blood) along the walls of blood vessels. Combinations of the foregoing are referred to herein generally as forms of plaque. Conventionally, narrowed blood vessels are widened or reopened by mechanical means such as angioplasty or atherectomy. These are invasive procedures. With atherectomy plaque is actually removed to enable less impeded blood flow. Atherectomy may be effected with a catheter system comprising a cutter blade for separation of the deposits, a system for dispersing the cut material, and an imaging system to guide catheter movement or aid in the cutting process. Generally, angioplasty and atherectomy are costly and complex procedures which create potential risks to the welfare of the patient. Moreover, the effectiveness of such procedures is limited, e.g., for treatment of coronary disease or blood vessels in the extremities. Nonetheless, because the build-up of deposits along the inner linings of vascular cavities causes life threatening medical problems, the benefits of using these methods are often seen to outweigh the risks. Yet, it remains desirable to provide a completely non-invasive technique which is effective, economical and without potential risk to the welfare of the patient.

BRIEF SUMMARY OF THE INVENTION

According to one series of embodiments there is provided a method for removing a deposit of plaque from a position along a wall of a blood vessel through which blood flows in a first direction. The method includes applying a magnetic field having a net direction predominantly orthogonal to the direction of the flow of blood through the vessel. In one implementation, a treatment method is provided where blood flows in a first direction through the blood vessel of a patient and the first direction may be orthogonal to an axis along which the patient is positioned for treatment. A magnetic field is applied which has a net field direction based on contributions from a plurality of components whose individual field strengths are variable so that the net field direction is selectable, i.e., not limited to a direction orthogonal to the axis along which the patient is positioned. This enables selection of a net field direction parallel with the axis along which the patient is positioned and selection of a net field direction predominantly orthogonal to the axis along which the patient is positioned. Treatment can thereby include provision of a magnetic field which is in a plane orthogonal to the direction of the flow of blood through the vessel.

A method for removing molecules in a layer of plaque from a position along a wall of a blood vessel through which blood flows in a first direction includes applying a magnetic field having a net direction predominantly orthogonal to the direction of the flow of blood through the vessel, the field being of sufficient strength to cause dissociation of a first molecule in the layer of plaque from another molecule in the layer, or from a molecule which forms the blood vessel wall, by severing a bond which otherwise stabilizes the position of the first molecule within the layer of plaque. In one implementation a treatment method is provided for removing molecules in a layer of plaque from a position along a wall of a blood vessel through which blood flows in a first direction through the blood vessel of a patient. The first direction may be orthogonal to an axis along which the patient is positioned for treatment. A magnetic field is applied which has a net field direction which is continuously variable and not limited to a direction predominantly determined by an axial field component parallel to the axis along which the patient is positioned. Accordingly, treatment can include selection of one or more magnetic field directions predominantly orthogonal to the direction of the flow of blood through the vessel. The field is of sufficient strength to cause dissociation of a first molecule in the layer of plaque from another molecule in the layer, or from a molecule which forms the blood vessel wall, by severing a bond which otherwise stabilizes the position of the first molecule within the layer of plaque.

There is also provided a method for removing molecules in a layer of plaque positioned along a wall of a blood vessel through which blood flows in a first direction. A magnetic field is applied which includes a component having a direction predominantly orthogonal to the direction of the flow of blood through the vessel. The field generates a Lorentz force, in response to which charge separation of conductive carriers in the blood results in an electric field which balances the Lorentz force. In one implementation of the method an orientation of a portion of the blood vessel under treatment is determined Based on the determined orientation, a magnetic field is applied which includes a component having a direction predominantly orthogonal to the direction of the flow of blood through the vessel.

A system is provided for removing plaque from a blood vessel. The system includes a plurality of winding configurations each positioned about a central axis along which a body region of a patient may be placed. Each winding configuration is designed to generate a magnetic field in a direction which passes through the body region. A first of the winding configurations is capable of generating a first magnetic field component perpendicular to a second magnetic field component generated by the second winding configuration.

According to another series of embodiments, a system is provided for removing plaque from a blood vessel. The system includes first and second components which generate a field and a C-arm configured to support the components in spaced apart relation while a patient is disposed between the components and along a first axis. A chassis supports the C-arm and the C-arm is moveable about the axis to rotate the components about the first axis.

In another method according to the invention molecules are removed in a layer of plaque from a position along a wall of a blood vessel through which blood flows in a first direction. An electric field is applied which has a net direction predominantly orthogonal to the direction of the flow of blood through the vessel. The field is of sufficient strength to dissociate a first molecule in the layer of plaque from another molecule in the layer, or from a molecule which forms the blood vessel wall, by severing a bond which otherwise stabilizes the position of the first molecule within the layer of plaque.

In still another method molecules are removed from in a layer of plaque positioned along a wall of a blood vessel through which blood flows in a first direction. An electric field is applied which has a component having a direction predominantly orthogonal to the direction of the flow of blood through the vessel, in response to which charge separation of conductive carriers in the blood results in an electric field.

BRIEF DESCRIPTION OF THE FIGURES

FIG. 1A is a partial perspective view of a blood vessel of a patient under treatment, illustrating a magnetic field and an electric field vector relative to a direction of a flow of blood through the vessel;

FIG. 1B is a view in cross section taken through a central axis of the blood vessel shown in FIG. 1A under a condition where plaque is formed completely around the vessel;

FIG. 2A illustrates a system for removal of plaque from the blood vessel of FIG. 1 according to a series of embodiments of the invention where an electric field which passes into or through the blood vessel is generated with one or more magnetic coils;

FIG. 2B illustrates a system for removal of plaque from the blood vessel of FIG. 1 according to another series of embodiments of the invention where an electric field which passes into or through the blood vessel is generated with field plates between which the field is created;

FIG. 3A illustrates a system for removal of plaque from a blood vessel according to another series of embodiments of the invention where an electric field which passes into or through the blood vessel of FIG. 1 is generated with one or more magnetic coils in a limited volume of the patient's body and which can be translated along and rotated about the body of the patient;

FIG. 3B illustrates system for removal of plaque from a blood vessel according to still another series of embodiments of the invention where an electric field which passes into or through the blood vessel of FIG. 1 is generated with field plates in only a limited volume of the patient's body;

FIG. 4A is a view in cross section of three pairs of double-helix coils in a system that allows adjusting a magnetic field vector to point in any direction;

FIG. 4B further illustrates the system of FIG. 4A wherein double helix coil windings are operable to rotate a magnetic field;

FIG. 5A is a view in cross section of coils in a system according to another embodiment that allow adjusting a magnetic field vector to point in any direction; and FIG. 5B illustrates the system of FIG. 5A according to still another embodiment wherein the coils are operable to rotate a magnetic field.

Like reference characters denote like elements throughout the figures and text.

DETAILED DESCRIPTION OF THE INVENTION

Before describing in detail exemplary systems and methods relating to the invention, it should be observed that, so as to not obscure the disclosure with details that will be readily apparent to those skilled in the art, certain conventional elements and steps have been presented with lesser detail, while the drawings and the specification describe in greater detail other elements and steps pertinent to understanding the invention. Also, the following embodiments are exemplary constructions which do not define limits as to structural arrangements or methods according to the invention. The embodiments are permissive rather than mandatory and are illustrative rather than exhaustive.

The compounds that constitute plaque along the walls of blood vessels are varied. Non-calcified plaques have been reported as comprising about 15 to about 35 percent cholesterol, which is an alcohol having a molecular composition of $C_{27}H_{45}OH$; and calcified plaques have been reported as comprising about 10 to about 30 percent cholesterol. Thus, a major component of plaque build-up in arteries is organic material.

Although the theory is not well established, build-up of plaque material, which may comprise a combination of organic and inorganic compounds, may relate to the presence of large molecular chain configurations characteristic of complex organic molecules and crystallization. Cholesterol molecules are carbon chains with substantially no significant electrical polarity or formal charges. It is believed that bonding of these molecules to each other or to the blood vessel walls is predominantly based on London dispersion forces. These attractive forces result when the electrons in atoms of two adjacent molecules occupy positions that form temporary dipoles. The bonds result when the momenta of the atoms or molecules are within a very narrow range. When the momenta are outside of this range, i.e., being either too small or too large, molecules in the flow do not bind together or with molecules which form the surrounding blood vessel walls. According to the invention, due to stringent requirements that momenta be within a limited range in order for the attractive forces to appear, bond formation between the adjacent molecules can be prevented and established bonds can be overcome with application of electromagnetic fields. That is, under the influence of a changing electrical potential, the process of bonding or aggregation of the molecules to form a thick layer of plaque can be hampered and any already existing weak bonds which otherwise stabilize a thick layer of plaque can be overcome thereby allowing the molecules to be carried away in the flow of blood.

A proposed understanding of this process is based on recognition that blood is a fluid having conductive constituents, plus other components some of which deposit to form plaque. Many of the constituents of blood are susceptible to magnetic fields. An electric field can be established by impressing a magnetic field across flowing blood. See FIG. 1A which provides a schematic view of a blood vessel through which a magnetic field is applied in accord with an embodiment of the invention. The magnetic field is generated in a direction perpendicular to the direction of the flow of blood and the direction of the resulting electric field is perpendicular to both the direction of the flow of blood and the direction of the magnetic field. This result, based on a magneto-hydrodynamic effect occurs because the blood, having a non-zero conductivity, flows through the magnetic field. Lorentz forces, which are perpendicular to both the direction of the blood flow and the direction of the magnetic field, act on the charge carriers in the liquid. Generally, the level of conductivity of the blood is a function of the concentration of red blood cells and certain electrolytes.

Under the influence of a proposed magnetic field, charge carriers in the flowing blood, resulting from dissociation, are displaced in the direction of the Lorentz forces. As charge carriers of opposite polarity migrate in different directions in response to the Lorentz forces, there is sufficient charge separation to create an electric field that counters the Lorentz forces. For a blood vessel having a 1 mm inside diameter, in which there is a blood flow velocity of one cm/sec in the presence of a magnetic flux density of about 0.1 Tesla, the charge separation of conductive carriers in the blood can balance with the Lorentz forces. This net charge separation results in a magneto-hydrodynamic voltage across the vessel which is on the order of a few microvolts. As best understood, the net electric field resulting from the Lorentz forces influences the association of the slightly polar or non-polar molecules which have accumulated along the wall of the blood vessel. That is, because these relatively large molecules are held together with a relatively low amount of binding energy, e.g., possibly caused by London Dispersion Forces, the relatively small magneto-hydrodynamic voltage is sufficient to cause dissociation of the molecules which form the plaque.

In one series of embodiments a magnetic system is provided which can prevent or reverse the build-up of plaque in tissue structures. Exemplary magnetic systems may generate pulsed or DC magnetic fields, e.g., ranging from 0.01 Tesla to several Tesla, or, in some embodiments in a range from less than 0.01 Tesla to more than several Tesla. There is also provided a completely non-invasive method for removing plaque from blood vessels in the heart and other parts of the human body, e.g., the brain. FIG. 1A provides a partial cut-away view of an exemplary blood vessel 2 having deposits of plaque 4 along an interior wall 6 thereof. A magnetic field 8 passes through the vessel 2. As further illustrated by the view in cross section of the blood vessel 2, shown in FIG. 1B, the magnetic field 8 is substantially perpendicular to the general direction 10 of blood flow. The resulting electric field 12 is perpendicular to both the direction 10 of blood flow and the magnetic field 8. The plaque 4 is shown in FIG. 1A to be predominantly only along one portion of the interior wall 6. It is to be understood that along other portions of the blood vessel, such as along the plane through which the view of FIG. 1B is shown, the plaque may cover the entire circumference of the interior wall 6.

Static or pulsed magnetic fields with flux densities in the desired range can be generated based on selection of appropriate coil designs and the level of current passed through the coils. In a magnetic system according to one series of embodiments, the direction of the field generated by these coils can be aligned as needed with respect to bloods vessel of interest. A system 20 configured for removal of plaque is shown in FIG. 2A. The system 20 comprises a pair of large Helmholtz coils 22 that can generate a field which surrounds substantially or entirely the whole body 16 of a patient 18. The Helmholtz coils 22 according to this example have a substantially circular shape and are parallel to one another. The coils 22 are symmetrically aligned with one another to produce a relatively uniform magnetic field 8 in a direction parallel to a central axis 24 along which the patient is positioned, i.e., in this example the axis 24 is in a direction extending from the head 26 to the feet 28 of the patient 18, and the axis 24 also passes through the center of the circular shape formed by each coil 22.

In other embodiments one or more magnetic coils of arbitrary shape may be arranged about the patient 18 to generate a magnetic fields in multiple orthogonal directions in order to assure that a magnetic field can be pointed in a direction which passes through one or more blood vessels of interest as shown for field 8 of FIG. 1B.

With reference to FIG. 3A, in another embodiment a system 30 comprises a smaller pair of Helmholtz coils 32 aligned in parallel with one another in a configuration similar to that shown for the embodiment of FIG. 2. The coils 32 are positioned to produce a desired magnetic field in only a limited volume of the patient's body 16. In this example the coils 32 are positioned about the patient's body to pass the magnetic field 8 through coronary blood vessels about the heart, e.g., the left main coronary artery, in order to remove plaque deposits 4 formed along the vessel walls 6. A feature of this embodiment is the ability to move the coils 32 of the system 30 along, for example, the axis 24 of the patient's body, and to rotate the magnetic field 8 around the axis in, for example, a plane which passes through the axis 24, while the field passes through the body 16 of the patient. The system 30 includes an electromechanical subsystem, details of which are not shown, comprising a conventional C-arm 34 which supports the magnetic coils 32 in spaced apart relation while a patient is disposed between the coils and along a central axis 24. The C-arm is moveable along the axis 24 to translate the coils 32 along a direction parallel to the axis 24. The C-arm is also moveable about the axis 24 to rotate the coils 32 about the axis 24. To effect such movements the C-arm is mounted on a moveable chassis 36 which may be displaced along a track (not shown) to provide movement of the coils 32 in directions parallel to the axis 24. The chassis 36 also permits rotational movement of the C-arm about the axis 24 in a conventional manner. The subsystem includes conventional motorized mechanisms (not shown) which provide automated translational and rotational movement of the C-arm. Although the coils 32 are illustrated as being relatively small in comparison to the coils 22 of the system 20 shown in FIG. 2A, the coils 32 of the system 30 may be relatively large with the system 30 performing the same afore described function but extending imposition of the magnetic field over a much larger portion of the patient's body 16 or over the entire length of the body 16. With such a mechanical arrangement it is possible to select a field orientation in any desired direction.

Implementation of the disclosed methods for removing plaque is facilitated by assuring that the direction of the magnetic field has a significant component perpendicular to the direction of blood flow through the blood vessels being treated. In order to effect removal of the plaque in a particular blood vessel in a human body, which vessel can extend in multiple directions, it is desirable that the system be capable of adjusting the magnetic field direction to provide a net field orientation approximately perpendicular to the blood vessel under treatment. As described for the embodiments of the systems 20 and 30, the direction of the magnetic field can be adjusted by moving the field generating coils, thereby adjusting the direction of the electric field created by charge separation.

As an alternative to physically rotating coils or other components to adjust the directions of the magnetic and electric fields, embodiments according to the invention may employ winding configurations which enable pointing of a magnetic or electric field vector in any direction without changing the physical orientation of the system components relative to the patient's body.

An example of a magnetic field winding configuration which generates such a rotatable field vector comprises a set of three superimposed coils or a set of three superimposed pairs of coils. Each coil or coil pair generates a magnetic field perpendicular to the field generated by the other two coils or coil pairs. One example configuration comprises two concentric pairs of double-helix coils positioned along a common axis (e.g., the axis 24 of FIGS. 2 and 3) which each generate a dipole field in a direction transverse to the common axis to the two coils. A third coil or pair of coils, concentric with the two double helix coils is used to generate a field in the direction of the common axis. The system thus has the capability of generating three field vectors, each in one of three orthogonal directions. By adjusting the currents in each coil set, a net field vector can be created in any direction. For a given field direction the magnitude of the field can also be adjusted by adjusting the currents in each of the coils appropriately. The three orthogonal magnetic field components can also be generated with three pairs of double helix coils, three pairs of saddle coils or three pairs of Helmholtz coils or combinations of these coil types. Moreover, individual ones of the desired field components can be generated with a single coil. By powering the individual coils or pairs of coils associated with each of the three field directions with a separately adjustable power supply, the coil currents can be temporally varied to generate a net field that dynamically changes in magnitude or rotates in direction. That is, by independently changing the current amplitudes and/or the current direction in the coils as a function of time, the field vector will move accordingly.

By way of example, FIGS. 4 and 5 provide examples in a series of embodiments where the direction of the magnetic field 8 can be rotated without rotating the spatial orientation of the coil systems which generate the component magnetic fields.

FIG. 4A is a view in cross section of an exemplary system 50 having a configuration in which three double helix coil winding sets 52, 54, 56 are operable to rotate the magnetic field 8 shown in FIG. 1. As further illustrated in the partial view of the system 50 shown in FIG. 4B, the winding sets 52, 54 and 56 are formed about an aperture 58 in which the patient 16 is positioned. A central axis 60 of the winding sets 52, 54 and 56 is shown to coincide with the central axis 24 of the body 18 when the patient is centrally positioned in the aperture 58 as shown in the figures. As indicated schematically in FIG. 4A, the coil set 52 comprises a pair of coils a,a', the coil set 54 comprises a pair of coils b, b' and the coil set 56 comprises a pair of coils c, c'.

Each of the three coil sets 52, 54, 56 may be separately powered to generate one of three magnetic field vectors, designated $B_{52}$, $B_{54}$ or $B_{56}$, each pointing in one specific direction. Accordingly, the system 50 includes three separate current supply controls: control 52s for coil set 52; control 54s for coil set 54; and control 56s for coil set 56. Each control can control the current level in each coil in the double helix pair which it powers.

The direction of the field vector generated by each pair of the double helix coils can be made orthogonal to the direction of the field vector generated by each of the other pairs of double helix coils. By modulating the relative current input to one or both of the coils in each coil pair, the magnitude of the magnetic field in each of three orthogonal directions can be adjusted to provide a desired field strength and net field direction. By superimposing three such fields of appropriate strengths, each generated by one of the three pairs of windings, net magnetic fields of desired strength and direction can be generated. The resulting field may be static, pulsed or time dependent in magnitude and direction and the field may be rotated as desired. For example, with respect to a central axis 10a, parallel to the direction 10 of blood flow in the vessel 2 of the patient body 16, a field of constant magnitude may be rotated 360 degrees about the vessel axis to remove the relatively weak bonds which bind individual molecules into the layer of plaque 4 along the wall 6 of the blood vessel 2.

Exemplary double helix coil designs suitable for this application are described in the following U.S. patent applications which are now incorporated herein by reference: U.S. Ser. No. 12/133,760 "Conductor Assembly Having An Axial Field In Combination With Quality Main Transverse Field", filed 5 Jun. 2008; and Ser. No. 12/061,782, "Wiring Assembly and Method For Positioning Conductor in a Channel Having a Flat Surface", filed 3 Apr. 2008. See, also, U.S. Pat. No. 6,921,042 also incorporated herein by reference.

The three coil sets of the system 50 surround a volume 62 within the aperture 58, in which the patient 18, or a portion of the body 16 of the patient, is positioned. The magnetic field 8, resulting from superposition of the magnetic field vectors $B_{52}$, $B_{54}$ or $B_{56}$, extends in a direction which is not necessarily orthogonal to the axis 24, but which can be positioned orthogonal to an arbitrary direction corresponding to the direction 10 of the flow of blood in the vessel 2 under treatment to remove the plaque 4. Thus, with reference also to FIG. 1, the system 50 generates a net magnetic field vector orthogonal to the axis 10a along the portion of any vessel 2 under treatment, i.e., in any arbitrary orientation with respect to the axis 24 and the central axis of the coil sets. In this simplified example and in other embodiments, the field source may be static or time varying, e.g., sinusoidal or pulsed.

FIG. 5A is a view in cross section of an exemplary system 70 having a configuration in which two double helix coil winding sets 52, 54, and a solenoid winding 76 are operable to rotate the magnetic field 8 shown in FIG. 1. As further illustrated in the partial view of the system 70 shown in FIG. 5B, the winding sets 52, 54 and the solenoid winding 76 are formed about an aperture 68 in which a patient is positioned. A central axis 80 of the winding sets 52, 54 and the solenoid winding 66 is shown to coincide with the central axis 24 of the body 18 when the patient is centrally positioned in the aperture 68 as shown in the figures. As indicated schematically in FIG. 5, the coil set 52 comprises a pair of coils a,a', the coil set 54 comprises a pair of coils b, b' and the coil 66 comprises a single solenoid coil.

Each of the two coil sets 52, 54 and the coil 66 may be separately powered to generate one of three magnetic field vectors, designated $B_{52}$, $B_{54}$ or $B_{66}$, each pointing in one specific direction. Accordingly, the system 50 includes three separate current supply controls: control 52s for coil set 52; control 54s for coil set 54; and control 66s for the coil 66. Each control 52s, 54s can control the current level in each coil in the double helix pair which it powers.

The vectors $B_{52}$ and $B_{54}$ are in a plane orthogonal to the axis 80 and the direction of the field vector generated by each pair of the double helix coils can be made orthogonal to the direction of the field vector generated by the other pair of double helix coils. The field vector $B_{66}$ is parallel with the axis 80. By modulating the relative current input to one or both of the coils in each coil set 52, 54 and the solenoid winding 56, the magnitude of the magnetic field in each of three orthogonal directions can be adjusted to provide a desired field strength and net field direction. By superimposing three such fields of appropriate strengths, each generated by one of the coil sets 52, 54 or the winding 56, net magnetic fields of desired strength and direction can be generated in the aperture 68. The resulting field may be static, pulsed or time dependent in magnitude and direction and the field may be rotated as desired. For example, with respect to a central axis 10a, parallel to the direction 10 of blood flow in the vessel 2 of the patient body 16, a field of constant magnitude may be rotated 360 degrees about the vessel axis to lyse the relatively weak bonds which form a layer of plaque 4 along the wall 6 of the blood vessel 2.

The three coil sets of the system 50 surround a volume 72 in which the patient 18, or a portion of the body 16 of the patient, is positioned. The magnetic field 8, resulting from superposition of the magnetic field vectors $B_{52}$, $B_{54}$ or $B_{56}$, extends in a direction which is not necessarily orthogonal to the axis 24, but which can be positioned orthogonal to an arbitrary direction corresponding to the direction 10 of the flow of blood in any vessel 2 under treatment to remove the plaque 4. Thus the system 50 generates a net magnetic field vector orthogonal to the axis 10a along the portion of any vessel 2 under treatment, i.e., in any arbitrary orientation with respect to the axis 24 and the central axis of the coil sets. In this simplified example and in other embodiments, the field source may be static, or time varying, e.g., sinusoidal or pulsed.

With regard to the several magnetic coil configurations which have been illustrated, it is noted that numerous other configurations can be assembled. For example, in lieu of the arrangement shown in FIGS. 2A and 3A, multiple pairs of Helmholtz coils can be assembled where each pair directs a magnetic field in a different direction about a region of a patient's body. Also, to effect generation of a magnetic field similar to that shown in FIG. 2A or FIG. 3A, the Helmholtz coil pair may be replaced with a single coil which may exhibit a less uniform field pattern but which nonetheless generates a field having a significant component orthogonal to the direction of blood flow within the vessel 2. That is, each of three component field vectors (e.g., similar to the component vectors $B_{52}$, $B_{54}$ and $B_{56}$) can each be generated with a single coil. Also, arrangements of two or three coils can be assembled in lieu of multiple pairs of Helmholtz coils to generate multiple magnetic field components, each in a different direction about a region of the patient's body. A gradient in the field, resulting from generating the components with single coils, may be advantageous. As one example, for a blood vessel which exhibits significant curvature, a somewhat non-uniform field may improve the ability to simultaneously provide magnetic field components, each of which can be orthogonal to a different direction of blood flow at each of two or more positions in the blood vessel.

Another series of embodiments according to the invention is based on recognition that the electric field, which facilitates severing of bonds between molecules in a layer of plaque, may be established without requiring generation of a magnetic field. While in some applications it may be advantageous to generate the electric field based on use of magnetic coils to create a Lorentz force, in other instances, in lieu of generating the magnetic field 8, an electric field can otherwise established across a blood vessel, e.g., in a direction orthogonal to the direction of blood flow. For example, a similar or identical result can be had by forming an electric potential across the blood vessel 2 with, for example, a pair of parallel plates. The field may be static or time varying, e.g., sinusoidal or pulsed. An advantage of generating the electric field without a magnetic field is that this can avoid creation of eddy currents which may be undesirable in, for example, tissue of the brain.

In this regard, FIG. 2B illustrates a system 20a having an arrangement analogous to the Helmholtz coil arrangement of FIG. 2A wherein the Helmholtz coils 22 are replaced with a pair of parallel plates 22a. A voltage may be applied across the plates 22a to establish a uniform electric field 8a between the plates. FIG. 3B illustrates a system 30a having an arrangement analogous to the configuration of FIG. 3A wherein, in lieu of incorporating the smaller pair of Helmholtz coils 32, the system 30a comprises relatively small parallel plates 32a aligned in parallel with one another in a configuration similar to that shown for the coils 32 of FIG. 2A, but with the coils 32a positioned to produce a desired electric field 8a in only a limited volume of the patient's body 16. In this example the plates 32a are positioned about the patient's body to pass the electric field 8a through blood vessels about the heart in order to remove plaque deposits 4 formed along the vessel wall 6. A feature of this embodiment is the ability to displace the plates 32a of the system 30a (e.g., along the axis 24 of the patient's body 16), and to rotate the electric field 8a around the axis 24 (e.g., in a plane which passes through the axis 24) while the electric field passes through the body 16 of the patient 18. The system 30a includes an electromechanical subsystem, details of which are not shown, similar or identical to that of the system 30, comprising a conventional C-arm 34 which translates the plates 32 along a direction parallel to the axis 24 and also rotates the plates 32a about the axis 34. The C-arm is mounted on a moveable chassis 36 which may be displaced along a track (not shown) to provide the movement in directions parallel to the axis 24. The chassis 36 also permits rotational movement of the C-arm about the axis 24 in a conventional manner. Conventional motorized mechanisms (not shown) provide for automated translational and rotational movement of the C-arm.

Although the plates 32a are illustrated as being relatively small in comparison to the plates 22a of FIG. 2B, the plates 32a of the system 30a may be relatively large with the system 30a performing the same aforedescribed function but extending imposition of the electric field over a much larger portion of the patient's body 16 or over the entire length of the body 16. With such a mechanical arrangement it is possible to select a field orientation in any desired direction.

The concepts disclosed for removal of plaque can be applied to specific blood vessels or segments of a blood vessel based on a determination of blood vessel orientation. For example, recognizing that blood vessels follow paths in many directions, orientation of a segment of a blood vessel under treatment can first be determined by conventional means such as use of two dimensional or three dimensional radiography techniques, including the techniques used for angioplasty or atherectomy. Accordingly, when applying the disclosed concepts to remove plaque from a segment of a specific blood vessel (e.g., a segment of a coronary blood vessel), an orientation of the segment is established to determine the direction of blood flow. Then, based on the determined orientation, a magnetic field is applied which includes a component having a direction predominantly orthogonal to the direction of the flow of blood through the vessel segment, the field generating a Lorentz force, in response to which charge separation of conductive carriers in the blood results in an electric field which balances the Lorentz force. Similarly, when applying the concepts with application of an electric field, e.g., with parallel plates such as shown in FIGS. 2B and 3B, the vessel orientation is first determined in order to orient the electric field in a direction which is orthogonal to the direction of the flow of blood through the segment of the vessel. More generally, when applying the concepts to treat blood vessels of multiple orientations, one may sequentially rotate the magnetic or electric fields to assure that the direction of the applied field is made orthogonal to the direction of blood flow in vessels of different orientations. In embodiments where the orientation of each vessel segment of interest is not first determined. The treatment procedure may include a field rotation through a large number of directions to assure that during the rotation each vessel segment of interest receives a field orthogonal to the direction of the flow of blood therethrough. In some arrangements field components may be established in three orthogonal directions about a limited region of interest or about the entire body of the patient with recognition that provision of field components of sufficient strength there is no need to predetermine the orientation of the vessel.

A feature of embodiments of the afore described treatment methods is that while the direction of blood flow through a vessel of interest may be orthogonal to an axis along which the patient is positioned for treatment, a magnetic field is applied which has a net field direction is variable and not limited to a direction predominantly determined by an axial field component parallel to the axis along which the patient is positioned. This feature is distinguished from what is achievable with prior art coil designs where the magnetic fields generated primarily exhibit axial field components, e.g., such as created with solenoidal windings along the direction in which a patient is positioned. That is, field configurations according to the invention depart from those generated in systems designed to generate a predominant or invariable axial field along the direction in which the patient is positioned, e.g., along the central axis 24. Thus treatment can include selection of a magnetic field direction which is predominantly orthogonal to the direction of the flow of blood through a vessel of interest. The orthogonal field is of sufficient strength to cause dissociation of a first molecule in the layer of plaque from another molecule in the layer, or from a molecule which forms the blood vessel wall, by severing a bond which otherwise stabilizes the position of the first molecule within the layer of plaque.

Also in accord with embodiments of the invention, a treatment method has been described which is not dependent on mechanical movement of field generating components in order to vary the net field direction. Recognizing that in removing a deposit of plaque from a position along a wall of a blood vessel in a patient through which blood flows in a first direction, the first direction may be orthogonal to an axis along which the patient is positioned for treatment, e.g., the axis 24, but according to embodiments of the invention the net direction of the applied magnetic field may be based on contributions from a plurality of components (e.g., two or three coils or coil sets) whose individual field strengths are variable. Consequently, the net field direction is selectable and not limited to a direction orthogonal to the axis along which the patient is positioned (e.g., the axis 24), this enabling both a selection of a net field direction parallel with the axis along which the patient is positioned and selection of a net field direction orthogonal to the axis along which the patient is positioned.

Consequently it can be assured that treatment can include provision of a magnetic field which is orthogonal to an arbitrary direction of flow of blood through a vessel of interest.

Although specific coil designs and plate geometries and methods have been illustrated for implementing concepts according to the invention, numerous other designs, geometries and methods are contemplated. For example, it is possible to provide rotating field configurations with one or more coils in configurations other than those of a double helix design, e.g., with a series of saddle coils or, as noted, with rotating Helmholtz coils. Further, although embodiments refer to arrangements where the fields are translated or displaced, it is also contemplated that the body of the patient under treatment may be moved along the direction of the axis 24 or rotated, e.g., in a plane, and that axial translation and rotation may be effected by combinations of movement of the fields and the patient.

The disclosed concepts and the invention as claimed are not limited to any particular theory. Further, there is no basis to conclude that the effects responsible for the prevention and removal of plaque from blood vessels will become inactive immediately upon removal of a magnetic or electric field. Rather, the effects responsible for the prevention and removal of plaque from blood vessels may be active for a significant period of time after the time at which the actual presence of the applied magnetic or electrical fields ceases. Part of this extended duration may be attributable to a weakening of the bonds between molecules of the accumulated plaque such that the plaque slowly assimilates into the blood stream.

While the invention has been described with reference to particular embodiments, it will be understood by those skilled in the art that various changes may be made and equivalents may be substituted for elements thereof without departing from the scope of the invention.

The invention claimed is:

1. A method for removing molecules in a layer of plaque from a position along a wall of a blood vessel through which blood flows in a direction, comprising:
applying an electric field to at least a portion of a person's body, wherein the electric field is produced by at least one external component to the body, the electric field having a net direction predominantly orthogonal to the direction of the flow of blood through the vessel, the field produced by the at least one external component being 0.01 Tesla to 5 Tesla of sufficient strength, without the need for an energy focusing device placed within the person's body, to dissociate a first molecule in the layer of plaque from another molecule in the layer, or from a molecule which forms the blood vessel wall, by severing a bond which otherwise stabilizes the position of the first molecule within the layer of plaque.

2. The method of claim 1 wherein the electric field is applied by generating a voltage between two plates.

3. The method of claim 1 wherein the electric field is a pulsed field.

4. A method for removing molecules in a layer of plaque positioned along a wall of a blood vessel through which blood flows in a direction, comprising:
applying a magnetic field to at least a portion of a person's body, wherein the magnetic field is produced by at least one external component to the body, the magnetic field including a component having a direction predominantly orthogonal to the direction of the flow of blood through the vessel, the field produced by the at least one external component being 0.01 Tesla to 5 Tesla of sufficient strength, without the need for an energy focusing device placed within the person's body, to cause charge separation of conductive carriers in the blood resulting in an electric field;
wherein said electric field alters association of non-polar molecules or slightly polar molecules which have accumulated along the wall of the blood vessel by providing energy greater than the energy which binds the molecules together thereby contributing to dissociation of the molecules and allowing the molecules to travel with the blood in the vessel.

5. The method of claim 4 wherein the applied magnetic field is a pulsed field.

6. The method of claim 5 wherein the electric field is applied in the absence of magnetic field.

\* \* \* \* \*